(12) United States Patent
Wyssen et al.

(10) Patent No.: US 12,376,882 B2
(45) Date of Patent: Aug. 5, 2025

(54) GYNECOLOGICAL DEVICE

(71) Applicant: ASPIVIX SA, Epalinges (CH)

(72) Inventors: Dany Wyssen, Bienne (CH); Julien Finci, Basel (CH); Frédéric Flahaut, Neuchâtel (CH); Anne Polikeit, Bienn (CH); Marion Aeby, Villars-sur-Glâne (CH); Luc Bergeron, Boussens (CH); Laurent Soldini, Lausanne (CH)

(73) Assignee: ASPIVIX SA, Epalinges (CH)

( * ) Notice: Subject to any disclaimer, the term of this patent is extended or adjusted under 35 U.S.C. 154(b) by 1154 days.

(21) Appl. No.: 17/284,213

(22) PCT Filed: Oct. 4, 2019

(86) PCT No.: PCT/EP2019/076857
§ 371 (c)(1),
(2) Date: Apr. 9, 2021

(87) PCT Pub. No.: WO2020/074369
PCT Pub. Date: Apr. 16, 2020

(65) Prior Publication Data
US 2021/0338284 A1 Nov. 4, 2021

(30) Foreign Application Priority Data
Oct. 9, 2018 (CH) .............................. CH01233/18

(51) Int. Cl.
*A61B 17/42* (2006.01)
*A61B 17/00* (2006.01)

(52) U.S. Cl.
CPC .............................. *A61B 17/4241* (2013.01);
*A61B 2017/00561* (2013.01); *A61B 2017/0084* (2013.01)

(58) Field of Classification Search
CPC ..... A61B 17/30; A61B 17/42; A61B 17/4241; A61B 17/442; A61B 2017/00561;
(Continued)

(56) References Cited

U.S. PATENT DOCUMENTS 5,865,827 A 2/1999 Bullister
2012/0283595 A1 11/2012 Curtis et al.

FOREIGN PATENT DOCUMENTS

GB 2485967 A 6/2012
WO 2016092458 A1 6/2016
WO WO-2017041849 A1 * 3/2017 .......... A61M 1/0007

OTHER PUBLICATIONS

International Search Report and Written Opinion issued Dec. 6, 2019, in International Appl. No. PCT/EP2019/076857.

* cited by examiner

*Primary Examiner* — Diane D Yabut
*Assistant Examiner* — Christian D Knauss
(74) *Attorney, Agent, or Firm* — MEDLER FERRO WOODHOUSE & MILLS PLLC

(57) ABSTRACT

A gynecological device including a body part having a vacuum chamber, a rod unit with distal and proximal ends, and a channel extending between the distal and proximal ends, a cervix head arranged at the distal end of the rod unit, and a sealing mechanism configured to switch between an ambient state and a vacuum state. The rod unit extends to the vacuum chamber of the body part with the proximal end of the rod unit being located in the vacuum chamber. The cervix head is configured to engage a vaginal side of a cervix. When in the ambient state of the sealing mechanism, the vacuum chamber is sealed and the channel of the rod unit is open to an exterior of the gynecological device. In the vacuum state of the sealing mechanism, the channel is open to the vacuum chamber and sealed to the exterior of the gynecological device.

19 Claims, 7 Drawing Sheets

(58) Field of Classification Search
CPC ...... A61B 2017/0084; A61B 2017/306; A61B 2017/308; A61B 2017/4225
See application file for complete search history.

GYNECOLOGICAL DEVICE

TECHNICAL FIELD

The present invention relates to a gynecological device according to the preamble of independent claim 1 and more particularly to a gynecological device for cervix handling.

Such device can be used for grasping and/or manipulating the cervix, for instance in connection with procedures of insertion or removal of intra uterine contraceptive devices.

BACKGROUND ART

Grasping cervix is essential in many very common gynecological procedures, among which the following can be mentioned by way of example: IUCD (intra uterine contraception device) insertion and removal; uterine tissue swab (endometrial) for diagnostic purpose; cervix dilatation for uterus cavity curettage; cervix dilatation for hysteroscopy (camera in uterus); measuring uterine cavity size during surgery; hysterosalpingography (imaging procedure of the uterine cavity and fallopian tubes for fertility check-up).

To execute the above procedures, practitioners use a speculum to open the vagina and view the cervix before inserting a tenaculum. The tenaculum is a forceps with two overlapping sharp hooks. After insertion into the vagina, the tenaculum allows grasping the external part of the cervix. Practitioners then pull the tenaculum jaws in the axis of the vagina. According to a natural anatomic configuration, the cervix is at an angle relative to a vaginal canal. By exerting traction, practitioners correct the anatomical physiological flexion angle, or kink, between the axis of the cervix and the body axis (uterus). Such a correction, of about 60°, is required to access the uterine cavity through the cervical canal. This angle modification minimizes the risk of uterine perforation during insertion of instruments into the uterine cavity.

However, traditional tenacula comprise teeth or prongs which are prone to tearing and/or piercing tissue during use. US 2012/0283595 A1 proposes an alternative tenaculum which employs uniformly distributed negative pressure. However, such solution uses a closed suction part with a form that renders the central tunnel too narrow and does not allow all instruments to enter or exit preventing the correct execution of some gynaecological procedures. In addition, the cervix dilation is limited by the central tunnel diameter, which is fixed.

GB 2 485 967 proposes an obstetric vacuum extractor comprising a cylinder; a cup communicating with the cylinder; and a piston movable within the cylinder to evacuate the cup; wherein the piston is movable within the cylinder by a handle connected to the piston by an extensible bias element permitting relative movement of the handle with respect to the piston.

None of the prior art devices, though, achieves by solid, uncomplicated technical means a gentle, non-traumatic handling of the cervix, while ensuring a perfect and effective grasping of the cervix.

WO 2016/092458 A1 discloses an apparatus for medical use comprising an improved suction pad technology in tight fluid connection, through a hollow rod, with a vacuum system. The vacuum system can be configured according to two different embodiments, respectively comprising a vacuum pump or a vacuum reserve source closed by a pierceable element designed to cooperate with a hollow needle.

However, it would be beneficial to incorporate in a gynecological device yet an alternative way to use vacuum for handling the cervix, which is even more straightforward and reliable than in the prior art applications. In fact, it would be preferable to even further simplify the fluido-mechanics involved. Moreover, it is desirable to enable an operator of the gynecological device to promptly and easily implement, even repeatedly or cyclically, steps of creation, activation, de-activation and/or re-creation of vacuum for cervix handling through a connected suction module. Offering the opportunity to reiterate the cervix handling procedures, up to the achievement of the desired effect, by repeatedly creating the desired vacuum conditions according to the treatment circumstances allows to perfectly complete the procedures by use of one same device.

Therefore, there is a need for a gynecological device allowing cervix handling in a safe and efficient way, without the aid of hazardous parts and relying on an economical, dependable technology. There is also the need for a gynecological device which, while single-use and advantageously not needing sterilisation, allows cervix handling also in multiple attempts, up to the perfect completion of the procedure.

DISCLOSURE OF THE INVENTION

According to the invention this need is settled by a gynecological device as it is defined by the features of independent claim 1. Preferred embodiments are subject of the dependent claims.

In particular, the invention deals with a gynecological device comprising a body part having a vacuum chamber; a rod unit with a distal end, a proximal end, and a channel extending between the distal end and the proximal end; a cervix head arranged at the distal end of the rod unit; and a sealing mechanism configured to switch between an ambient state and a vacuum state.

The body part can protect the mechanical system formed by the rod unit and the sealing mechanism and may guarantee the airtightness of the vacuum chamber. The body part is preferably configured to allow a firm grip of the gynecological device during manipulation thereof by an operator or practitioner.

The rod unit extends to the vacuum chamber of the body part such that the proximal end of the rod unit is located in the vacuum chamber of the body part. By extending into the vacuum chamber the rod unit can be securely connected to the body part. In particular, such arrangement allows for providing the activatable pressure connection between the vacuum chamber and the channel of the rod unit.

The term "distal" as used herein relates to a direction towards a front end of the gynecological device or towards an end which, in use, is to be oriented or directed to a patient. In particular, the front end of the device can be formed by the cervix head and, more specifically, an edge of the cervix head. Analogously, the term "proximal" as used herein relates to a direction opposite distal, i.e. a direction towards a back end of the device or an end which, in use, is to be oriented away from the patient to a practitioner operating the device.

The cervix head is configured to engage a section of a cervix from a vaginal side. The cervix head can have a chamber with an edge. Advantageously, the chamber can be put in fluid connection with the channel of the rod unit. The edge of the chamber can form the distal end of the device and can be formed such that it essentially corresponds to the shape of the cervix. In particular, viewed form the distal end side, the edge can be a closed loop in form of a C. Like this, the cervix head can be positioned at the cervix near around the external orifice opening such that this opening still is accessible.

In the ambient state of the sealing mechanism, the vacuum chamber of the body part is sealed and the channel of the rod unit is open to an exterior of the gynecological device, whereas in the vacuum state of the sealing mechanism, the channel of the rod unit is open to the vacuum chamber of the body part and sealed to the exterior of the gynecological device.

The term "exterior" used in connection with the gynecological device relates to a space outside or around the device. Thereby, for being connected to the exterior an element can be in direct or indirect contact or connection with the outside. Typically, outside or surrounding the device there is an ambient or atmospheric pressure such that when being open to the exterior any under- or over-pressure in the channel or in the vacuum chamber is eliminated.

The term "open" in connection with the vacuum chamber, the channel and the exterior relates to being in connection such that a pressure difference can be compensated. In particular, open can be in fluid or air connection.

By being equipped with a sealing mechanism as above described, the gynecological device can be actively switched between the ambient state and the vacuum state. This arrangement makes the device capable of generating a vacuum inside the vacuum chamber, i.e. in the ambient state, and then allows the device to change to being capable of applying a vacuum at the cervix head when being set to the cervix via the vagina, i.e. in the vacuum state, and to further change to being capable of releasing the cervix head from the cervix by eliminating the vacuum in the cervix head, i.e. in the ambient state again. This allows for a very sophisticated and convenient operation of the device, in particular for gripping and pulling the cervix in a gynecological application, also in multiple successive phases wherein the procedure is progressively perfected up to the desired completion.

The arrangement of the gynecological device according to the invention allows for providing the complete device as a disposable. In particular, the design of the device allows to use procedures and materials in manufacture such that the gynecological device can be provided at comparably low costs. This allows for a single use or few use application of the device.

Furthermore, the arrangement of the gynecological device according to the invention allows for providing some components to be multi-used or permanent used and others to be single used or few used. In particular, the gynecological device can be arranged such that the cervix head is exchangeable and the other components such as the body part, rod unit and the like form a reusable instrument. Like this, the cervix head can be disposed after usage whereas the main parts of the device can be reused. Such exchangeable cervix head also allows for efficiently adapting the device to the needs and anatomical conditions given.

Preferably, the sealing mechanism comprises a sleeve element arranged in the vacuum chamber of the body part, the rod unit extending through the sleeve element. The sleeve element can be made axially movable relative to the vacuum chamber and relative to the rod unit. The term "axially movable" as used in this connection can relate to a movement along an axis of the rod unit or along an axis of the overall, complete device. Thus, the rod unit and/or the gynecological device can have an advantageously central and straight axis which favors this movement.

Thereby, the sleeve element allows for efficiently implementing a switching between ambient and vacuum states. In particular, by moving the sleeve along the axis, the two states can efficiently and reversibly be achieved. For example, the sleeve can slide on the rod unit and/or in the vacuum chamber along the axis such that the switching motion is well guided and predefined.

Preferably, the sleeve element of the sealing mechanism has an internal seal member sealing the sleeve element and the rod unit towards each other.

Moreover, preferably the sleeve element of the sealing mechanism has an external seal member sealing the sleeve element and the vacuum chamber of the body part towards each other.

Preferably, a first friction force between the internal seal member of the sleeve element of the sealing mechanism and the rod unit is smaller than a second friction force between the external seal member of the sleeve element of the sealing mechanism and the vacuum chamber. For achieving this, a friction reduction substance such as silicone oil or the like can be provided between the internal seal member of the sleeve element of the sealing mechanism and the rod unit. For example, such substance can be sprayed into the sleeve element. An axial movement of the rod unit in a direction towards a distal or front end of the gynecological device (that is, towards an end which, in use, is to be oriented or directed to a patient) corresponds to a traction of the cervix head, for instance imparted by an operator by pulling. Such displacement, in combination with the above friction force arrangement, allows for an initial vacuum creation within the vacuum chamber of the body part. More precisely, it initiates and enables the creation of two distinct chambers within the body part at two respective differential pressures, one of which is the vacuum chamber. The vacuum chamber can be disposed proximally with respect to a distinct, more distal chamber within the body part which is instead held at a higher pressure, for instance corresponding to an ambient or atmospheric pressure. The traction of the cervix head can cause a translation of the rod unit within the body part as well as relative to the sealing mechanism. The sealing mechanism can be kept still, in this phase, due to the higher second friction force between the external seal member of the sleeve element of the sealing mechanism and the vacuum chamber, or otherwise said, the walls of the body part. Therefore, the friction force arrangement of the internal seal member and of the external seal member of the sleeve element as above explained is functional to the initial vacuum generation and creation of the vacuum chamber within the body part.

For this purpose, preferably, the internal seal member and the external seal member of the sleeve element of the sealing mechanism are axially offset from each other.

Preferably, the internal seal member of the sleeve element of the sealing mechanism is closer to the distal end of the rod unit than the external seal member of the sleeve element of the sealing mechanism.

After the initial generation of vacuum within the vacuum chamber, further application of a traction force on the cervix head, for instance by pulling, carries the rod unit and the sleeve element of the sealing mechanism together, up to completion of the vacuum generation in the ambient state of the sealing mechanism.

Upon generation of vacuum in the vacuum chamber, as above described, in the ambient state of the sealing mechanism, the sleeve element is preferably axially moved in a first position in which the internal seal element seals the channel of the rod unit and the vacuum chamber of the body part towards each other, and the external seal element seals the vacuum chamber of the body part towards the exterior of the gynecological device.

On the other hand, upon activation of the vacuum of the vacuum chamber, that is in the vacuum state of the sealing mechanism, the sleeve element is preferably axially moved in a second position, for instance more distal to the first position, in which the internal seal element seals the channel of the rod unit towards the exterior of the gynecological device, and the external seal element seals the vacuum chamber of the body part towards the exterior of the gynecological device. Thus, the vacuum can be transferred from the vacuum chamber all the way to the cervix head, through the channel of the rod unit, for optimal cervix grasping and handling.

Preferably, for the switching from the first position of the ambient state to the second position of the vacuum state, the sleeve element comprises an activation part extending to an exterior of the body part.

The rod unit can essentially comprise a portion of elongated shape. Thereby, this portion can be cylindrical with a circular, oval or polygonal cross section. Also, it can be essentially straight. The elongated portion of the rod unit can further be equipped at its circumference with additional elements such as reinforcement elements, guidance elements or the like. Preferably, the rod unit has a projection configured to abut the sleeve element when the rod unit is moved in a distal direction along its axis through the sleeve element. The projection of the rod unit can be positioned such that that the rod unit is movable to a predefined extent along its axis through the sleeve element. In particular, such predefined extent of axial movement can allow for providing moving the internal and external seal elements in order to change the sealing mechanism from the ambient state to the vacuum state and vice versa.

Preferably, the rod unit has a lateral through hole open to the channel of the rod unit. Such lateral through hole can further cooperate with the internal and external seal elements in order to change the sealing mechanism from the ambient state to the vacuum state and vice versa. Namely, the relative position of the seals and of the through hole can be calibrated in a way that, in the ambient state the through hole is put in fluid communication with the exterior of the gynecological device; whereas in the vacuum state the through hole is put in fluid communication with the vacuum chamber.

The gynecological device according to the present invention can comprise a cap closing the channel of the rod unit at the proximal end of the rod unit. The cap is preferably dimensioned not to fit into the sleeve element of the sealing mechanism. Thus, the cap can abut the sleeve element such that it prevents the rod unit to be completely withdrawn from the sleeve element.

Preferably, a locking mechanism is provided which is configured to switch between a released state in which the rod unit is axially movable relative to the vacuum chamber and a locked state preventing movement of the rod unit into the ambient state. Such prevention of movement of the rod unit in the locked state can, e.g., be embodied by the rod unit being axially immovable relative to the vacuum chamber. Such lock mechanism advantageously prevents the rod unit from being sucked back to its initial position by the created vacuum of the vacuum chamber. The vacuum generation, in fact, implies an altered force distribution within the body part which would otherwise pull the rod unit back to its initial position, in a proximal direction.

More specifically, in the released state of the locking mechanism, the rod unit is preferably axially movable relative to the vacuum chamber of the body part such that a vacuum is generated inside the vacuum chamber when the rod unit is distally moved relative to the vacuum chamber.

The locking mechanism can be configured such that pivoting the rod unit about its longitudinal axis in one direction switches the locking mechanism into the locked state, whereas pivoting the rod unit about its axis in another opposite direction switches the locking mechanism into the released state.

The locking mechanism can comprise notches integral to the rod unit which are configured to engage with corresponding elements of the gynecological device, for instance female elements on a front cap closing the body part.

Preferably, the gynecological device is configured to open the though hole to the vacuum chamber when being in the locked state. Like this, the vacuum can be activated, i.e. applied though the through hole, the channel and the cervix head.

Thereby, the gynecological device preferably is configured to open the through hole by applying a push force to the cervix head. Also, the though hole preferably is open to the vacuum chamber when being in the released state. Such configuration allows for conveniently applying the vacuum once the cervix head is appropriately positioned. Also such configuration allows for providing the device with a comparably small numbers of parts since no manual activation parts are required.

Preferably, the gynecological device can be arranged in a pre-operation state in which the rod unit is moved to a maximum extent in a proximal direction into the vacuum chamber of the body part. In such pre-operation state, the device can be comparably compact such that it is convenient to supply and store. Further, in this state the rod unit can be protected inside the body part, such that the risk of damaging the relatively sensible rod unit can be minimized.

Preferably, the vacuum chamber of the body part has a main section and a proximal section, wherein the main section has a first diameter and the proximal section has a second diameter being bigger than the first diameter. The proximal section of the vacuum chamber can be created, by way of example, within a back cap portion configured to proximally close the body part. The bigger diameter of the back cap can make easier the gripping of the device by an operator, for instance during traction of the cervix head.

In the above arrangement, having a narrower main section and a larger proximal section of the vacuum chamber, the external seal member is compressed when being positioned in the main section of the vacuum chamber of the body part, while the external seal member is non-compressed when being positioned in the proximal section of the vacuum chamber of the body part. Like this, when the device is stored and supplied, the external seal member can be held expanded in the larger proximal section of the vacuum chamber such that its durability can be increased.

In order to ensure that the second friction force between the external seal member of the sleeve element of the sealing mechanism and the vacuum chamber is larger than the first friction force between the internal seal member of the sleeve element of the sealing mechanism and the rod unit, an inclined transition section between the proximal section of the vacuum chamber of the body part and the main section of the vacuum chamber of the body part can be created, having a diameter decreasing from the second diameter to the first diameter. Such an inclined transition section, for instance in the form of an inclined plan taperedly transitioning from the larger second diameter to the reduced first diameter. Different inclination can be designed to achieve different friction forces. Alternatively, the transition section between the proximal section of the vacuum chamber of the body part and the main section of the vacuum chamber of the body part can be obtained by defining a radius on the inner diameter edge of the main section.

BRIEF DESCRIPTION OF THE DRAWINGS

The gynecological device according to the invention is described in more detail herein below by way of an exemplary embodiment and with reference to the attached drawings, in which.

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
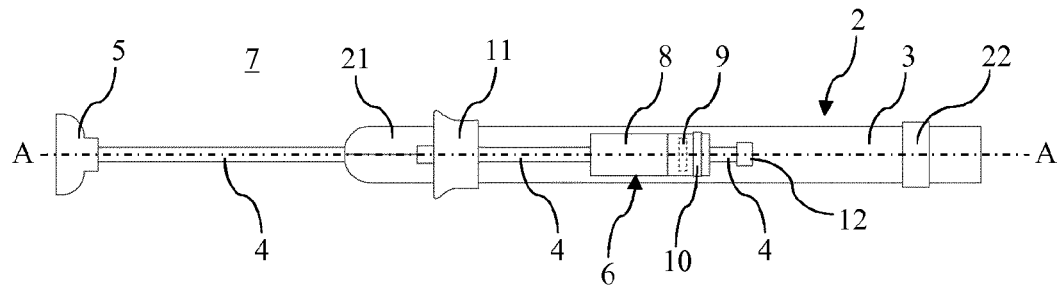
FIG. 1 shows a schematic section view of a first embodiment of the gynecological device according to the present invention.

With reference to FIG. 1, a first embodiment of a gynecological device 1 according to the present invention comprises a body part 2 having a vacuum chamber 3. Vacuum can be generated in the vacuum chamber 3 during operation of the device 1. The gynecological device 1 further comprises a rod unit 4 with a distal end, a proximal end and a channel 41 extending between the distal end and the proximal end. The rod unit 4 extends to the vacuum chamber 3 of the body part 2 such that the proximal end of the rod unit is located in the vacuum chamber 3. The rod unit 4 is essentially cylindrical and has a straight shape. The term "essentially cylindrical" in this context does also cover some deviations from a geometrical cylindrical shape. In particular, it does also cover cylinders provided with additional elements such as reinforcement elements or guidance elements as visible in FIG. 7. The channel 41 is straight along the rod unit 4. The rod unit 4 is designed to resist to the mechanical stresses applied during manipulation of the cervix by an operator using the device 1.

A cervix head 5, configured to engage a section of a cervix from a vaginal side and to conform to its anatomy, is arranged at the distal end of the rod unit 4, in a way that the cervix head 5 is in fluid communication with the channel 41. The rod unit 4 therefore guarantees that vacuum created in the vacuum chamber 3 inside the body part 2 can be transferred to the cervix head 5 contacting the cervix.

The body part 2 of the gynecological device 1 also comprises a back cap 22, closing the substantially tubular body part 2 and proximally guaranteeing air tightness at a back end of the body part 2. The back cap 22 is also configured to be easily grippable by an operator or practitioner when using the device 1. For this purpose, for instance, the back cap 22 can have a bigger diameter than the rest of the body part 2. Additionally or alternatively, the back cap 22 can be provided with a wing-like structure or an extended finger flange structure to facilitate traction, if needed.

The rod unit 4 can be extracted and re-positioned inside the body part 2 by way of a translation movement. The body part 2 further comprises a front cap 21 distally partially closing a front end of the device 1. The front cap 21 which cooperates with the rod unit 4 to guide the translation movement of the rod unit 4 as well as to eventually lock the position of the rod unit 4 once extended.

A sealing mechanism 6 is configured to switch between an ambient state and a vacuum state. As exemplified in FIG. 2, in the ambient state of the sealing mechanism 6, the vacuum chamber 3 is sealed and the channel 41 of the rod unit 4 is open to an exterior 7 of the gynecological device 1. Instead, in the vacuum state of the sealing mechanism 6, the channel 41 of the rod unit 4 is open to the vacuum chamber 3 of the body part 2 and sealed to the exterior 7 of the gynecological device 1.

In order to alternatively put the channel 41 of the rod unit 4 in connection with the exterior 7 or with the vacuum chamber 3, the rod unit 4 is provided with a lateral through hole 42 open to the channel 41. Like this, respectively the pressure in the channel 41 equals that of the exterior 7 when in the ambient state or that of the vacuum chamber when in the vacuum state.

A cap 12, which can take the form of a piston head, closes the channel 41 of the rod unit 4 at the proximal end of the rod unit 4.

The sealing mechanism 6 comprises a sleeve element 8 arranged in the vacuum chamber 3 of the body part 2. The rod unit 4 extends through the sleeve element 8. The sleeve element 8 is axially movable relative to the vacuum chamber 3 and relative to the rod unit 4 along the axis A-A of the rod unit 4. The axis A-A in this case substantially coincides with the axis of the complete gynecological device 1.

The cap 12 is dimensioned not to fit into the sleeve element 8 of the sealing mechanism 6, preventing the decoupling of rod unit 4 and sleeve element 8.

Figure 2:
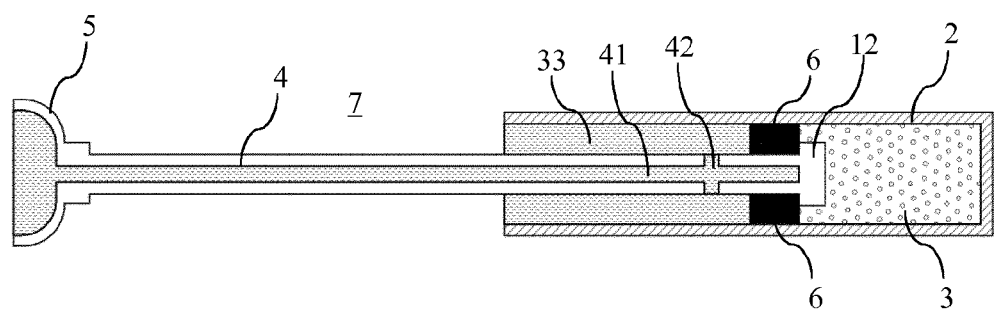
FIG. 2 shows two schematic section views of the gynecological device of FIG. 1, aimed at illustrating the general functioning principle thereof.
Figure 2:
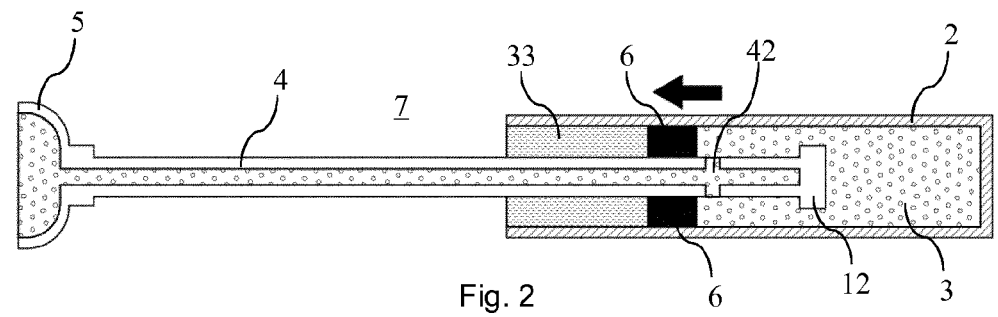
Figure 3:
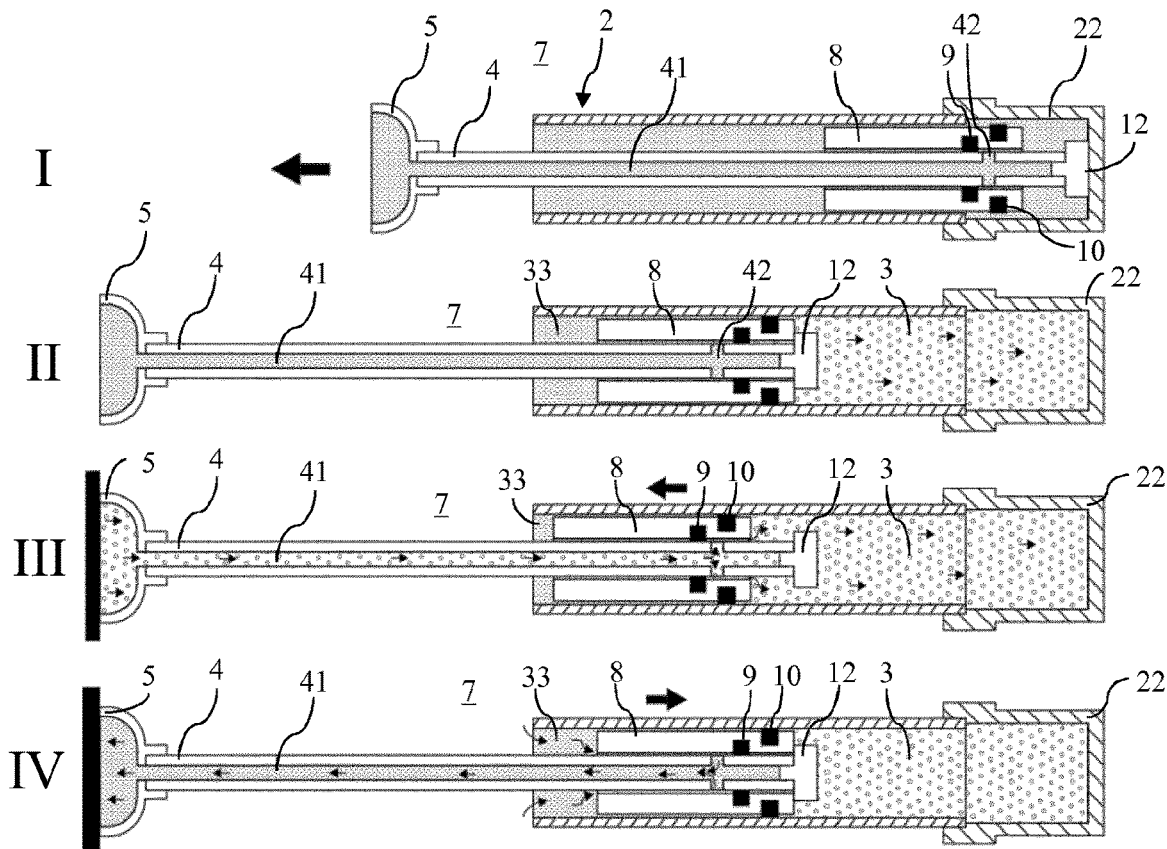
FIG. 3 shows four schematic section views of the gynecological device of FIG. 1, aimed at illustrating a full functioning cycle thereof.

Thus, as shown in FIG. 2 and more in detail in FIG. 3, the axial movement of the sleeve element 8 allows to implement a reversible switching between the ambient state of the sealing mechanism 6, for generation of a vacuum in the vacuum chamber 3, and a vacuum state of the sealing mechanism 6, for transfer of the generated vacuum to the cervix head 5. As the volume of the chamber 3 is increasing in the vacuum chamber 3, the vacuum accordingly increases and the remaining internal volume of the body part 2 decreases. Substantially, the vacuum generation implies proximally the formation, within the volume of the body part 2, of the vacuum chamber 3, while laterally a corresponding definition of a separate, residual chamber 33. Both in the ambient state and in the vacuum state as defined, the residual chamber 33 remains open to the exterior 7 of the gynecological device 1.

In FIG. 3, it is shown the passage from an initial configuration of the gynecological device 1 when just out of a packaging, at point I, before traction of the cervix head 5, to the completion of a cervix head handling procedure and the consequent release of a vacuum generated within the device, at point IV. The configurations at points II and III of FIG. 3 substantially correspond respectively to the ambient state and to the vacuum state of FIG. 2 as above described. The configuration of the gynecological device 1 just out of the packaging can also be designated as pre-operation state. In the pre-operation state, the rod unit 4 is moved to a maximum extent in a proximal direction into the vacuum chamber 3 of the body part, for the sake of compactness during transport and storage and for protecting the more delicate mechanics.

FIG. 3 also specifies further elements of the sealing mechanism 6 which can contribute to the swift switching between ambient and vacuum states. In fact, the sleeve element 8 of the sealing mechanism 6 has an internal seal member 9 sealing the sleeve element 8 and the rod unit 4 towards each other.

Moreover, the sleeve element 8 of the sealing mechanism 6 has an external seal member 10 sealing the sleeve element 8 and the vacuum chamber 3 of the body part 2, or generally the internal walls of the body part 2, towards each other.

The internal seal member 9 and the external seal member 10 of the sleeve element 8 of the sealing mechanism 6 are axially offset from each other along the axis (A-A). Namely, the internal seal member 9 of the sleeve element 8 of the sealing mechanism 6 is closer to the distal end of the rod unit 4 than the external seal member 10 of the sleeve element 8 of the sealing mechanism 6. This disposition of the seal members 9, 10, in combination with the displacement of the rod unit 4 and a consequent positioning of the lateral through hole 42, as well as with the calibrated axial movement of the sleeve element 8, allows to precisely achieve the abovementioned ambient and vacuum states, as portrayed in FIG. 3 at points II and III.

In FIG. 3 at point II it is shown how, in the ambient state of the sealing mechanism 6, the sleeve element 8 is axially moved in a first position in which the internal seal element 9 seals the channel 41 of the rod unit 4 and the vacuum chamber 3 of the body part 2 towards each other, while the external seal element 10 seals the vacuum chamber 3 of the body part 2 towards the exterior 7 of the gynecological device 1.

In FIG. 3 at point III it is shown how, in the vacuum state of the sealing mechanism 6, the sleeve element 8 is axially moved in a second position in which the internal seal element 9 seals the channel 41 of the rod unit 4 towards the exterior 7 of the gynecological device 1, and the external seal element 10 seals the vacuum chamber 3 of the body part 2 towards the exterior 7 of the gynecological device 1.

In order for the sleeve element 8 to reach the second position of FIG. 3 at point III from the first position at point II, the sleeve element 8 is substantially slid forward, so that the lateral through hole 42 is in between internal seal element 9 and external seal element 10. The vacuum, previously created in chamber 3 at point II, is then activated at point III, reaching the cervix head 5. At this stage, an operator can hold, pull and manipulate the cervix.

By sliding back the sleeve element 8, at point IV of FIG. 3, the lateral through hole 42 is brought back to a position relative to the seals 9,10 equivalent to the one occupied at point II, substantially bringing back the channel 41 of the rod unit 4 to being open to the exterior 7. At point IV of FIG. 3 the vacuum is released from inside the cervix head 5 and the rod unit 4, which are brought at a pressure equilibrium with the residual chamber 33, open to the exterior 7 i.e. to an atmospheric pressure.

A first friction force between the internal seal member 9 of the sleeve element 8 of the sealing mechanism 6 and the rod unit 4 is smaller than a second friction force between the external seal member 10 of the sleeve element 8 of the sealing mechanism 6 and the vacuum chamber 3.

Figure 3A:
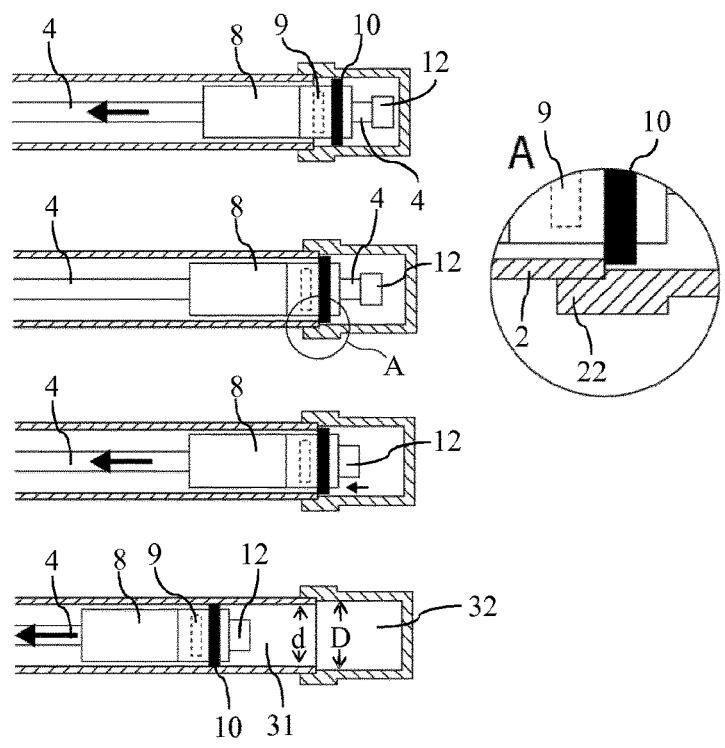
FIG. 3A shows further four schematic views, partially cut, of the gynecological device of FIG. 3, wherein the first two schematic section views of FIG. 3 are further split into intermediate sub-steps.

The above friction force distribution allows to bring the device 1 from the initial position of the device 1 just out of packaging portrayed at point I of FIG. 3, as well as at the beginning of the sequence of FIG. 3A—to the formation of the vacuum chamber 3, while laterally defining the separate, residual chamber 33, within the volume of the body part 2.

FIG. 3A specifies intermediate steps comprised between the abovementioned initial position out of the packaging, or pre-operation state, and the ambient state of FIG. 3 at point II. At first, by pulling the cervix head 5 and the rod unit 4, both the rod unit 4 and the seal mechanism 6 move together within the back cap 22 up to the narrower section of the body part 2. Subsequently, thanks to the above differential friction forces, the seal mechanism 6 does not move and only the rod unit 4 translates, allowing to create two separate chambers 3, containing the vacuum, and 33, open to the exterior 7 of the device 1. By further pulling, the seal mechanism 6 and the rod unit 4 again move integrally to increase the volume of the vacuum chamber 3 and generate the required vacuum.

As it can be appreciated from the fourth of the section views of FIG. 3A and from the enlarged detail of the second of the section views in FIG. 3A, the vacuum chamber 3 of the body part 2, thanks to the design of the back cap 22 relative to the rest of the body part 2, comes to have a main section 31 and a proximal section 32, wherein the main section 31 has a first diameter d and the proximal section 32 has a second diameter D which is bigger than the first diameter d.

As a consequence of the above design, the external seal member 10 comes to be compressed when being positioned in the main section 31 of the vacuum chamber 3 of the body part 2, and the external seal member 10 is instead non-compressed when being positioned in the proximal section 32 of the vacuum chamber 3 of the body part 2. Stress is therefore avoided on the external seal member 10 when unneeded, that is during shelf life, ensuring that the seal will on the other hand perform appropriately when the device 1 is in use.

Moreover, in order to secure a friction force on the external seal member 10 larger than on the internal seal member 9 for the purpose of initial vacuum, chamber 3 formation and separation from the residual chamber 33, not only the geometry of the seal member 10 can be purposely chosen, but also an inclined transition section can be created between the proximal section 32 of the vacuum chamber 3 of the body part 2 and the main section 31 of the vacuum chamber 3 of the body part 2. Thus, a diameter of the internal walls of the body part 2 decreases from the second diameter D to the first diameter d. Several geometries and angles are possible for the above inclined plan of the inclined transition section, calibrated to different resulting friction forces. Alternatively, also a radius on the inner diameter edge of the main section 31 can be created, to create a friction force variation.

Figure 5:
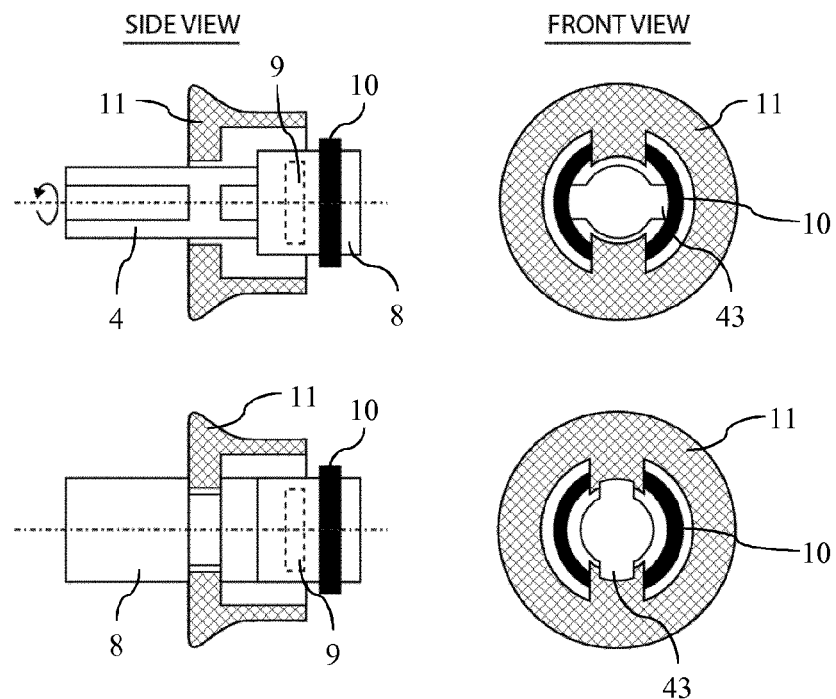
FIG. 5 shows an embodiment for an activation part of a sleeve element of a sealing mechanism of the gynecological device of FIG. 1.

In order to slide forward, in a distal direction, the sleeve element 8 from the first position at point II of FIG. 3 to the second position at point III of FIG. 3, the sleeve element 8 is provided with an activation part 11, for instance in the form of a slider, which extends to an exterior of the body part 2, as shown in FIG. 5. The slider 11 can be guided by the front cap 21, on which it slides. Further, the front cap 21 can be provided with clips 21* designed to click fit with the slider 11, so that the slider 11 is mechanically locked in a position which allows the vacuum state to be established and maintained during the cervix manipulation procedure. A couple of pressable clips 21* can be provided on opposite sides of the front cap 21, designed to be pressed by the operator simultaneously to allow sliding back, in a proximal direction, of the slider 11, once that the cervix manipulation procedure is concluded and it is desired to release or de-activate the vacuum.

In FIG. 5 it is shown how the rod unit 4 has a projection 43 configured to abut the sleeve element 8 when the rod unit 4 is moved in a distal direction along its axis A-A through the sleeve element 8. In particular, when the rod unit 4 is moved completely in a distal direction allong its axis A-A, the sleeve element 8 is in abutment with the front cap 21. This abutment ensures that the user is at the correct position to turn the rod unit 4 by 90° and lock the position as described below.

The projection 43 of the rod unit 4 is positioned such that the rod unit 4 is movable to a predefined extent along its axis A-A through the sleeve element 8.

Figure 4:
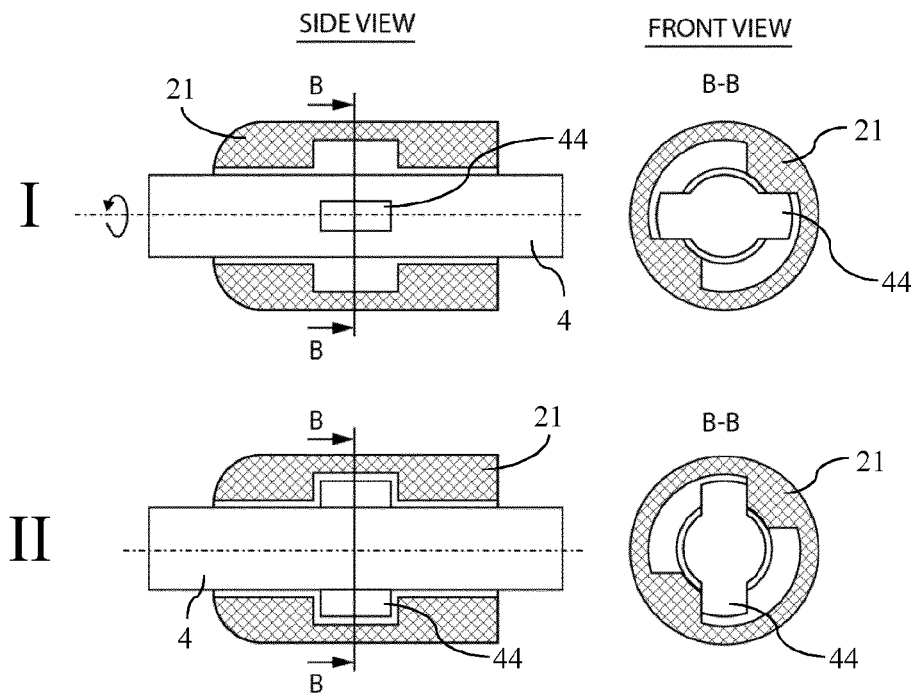
FIG. 4 shows first side and frontal section views and second side and frontal section views of an embodiment for a locking mechanism of a rod unit of the gynecological device of FIG. 1, respectively in a released and in a locked state of the locking mechanism.

In FIG. 4, a locking mechanism for the rod unit 4 is shown. The locking mechanism is configured to switch between a released state, represented at point I of FIG. 4., in which the rod unit 4 is axially movable relative to the vacuum chamber 3; and a locked state, represented at point II of FIG. 4, in which the rod unit 4 is axially immovable relative to the vacuum chamber.

The locking mechanism is created by the cooperation of protrusions 44 on the rod unit 4 which, while free to slide within the front cap 21 when in the released state, engage instead in corresponding female recesses of the front cap 21 when in the locked state, preventing the rod unit 4 from translating either in a distal or in a proximal direction. Thus, in the locked state, the rod unit 4 stays fixed, while the vacuum is activated, and does not translate back to its initial position as it would instead tend to do, owing to the force exerted by the vacuum which is established in the vacuum chamber 3.

The locking mechanism created by the protrusions 44 and the corresponding female recesses in the front cap 21 is configured such that pivoting the rod unit 4 about its longitudinal axis A-A in one direction switches the locking mechanism into the locked state, whereas pivoting the rod unit 4 about its axis in another opposite direction switches the locking mechanism into the released state.

FIGS. 6 to 11 show consecutive steps of a cycle of use of the gynecological device 1.

Figure 6:
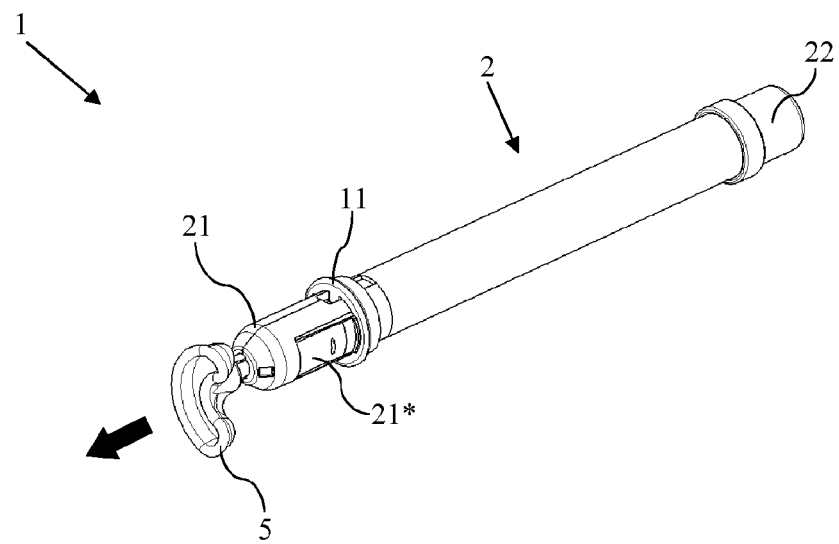
FIG. 6 shows a step of creating a vacuum in the gynecological device of FIG. 1 by traction of a cervix head thereof and translation of the rod unit in a distal direction out of a body part of the gynecological device.

FIG. 6 shows a step of creating a vacuum in the gynecological device 1 by traction of the cervix head 5 and translation of the rod unit 4 in a distal direction out of the body part 2.

Figure 7:
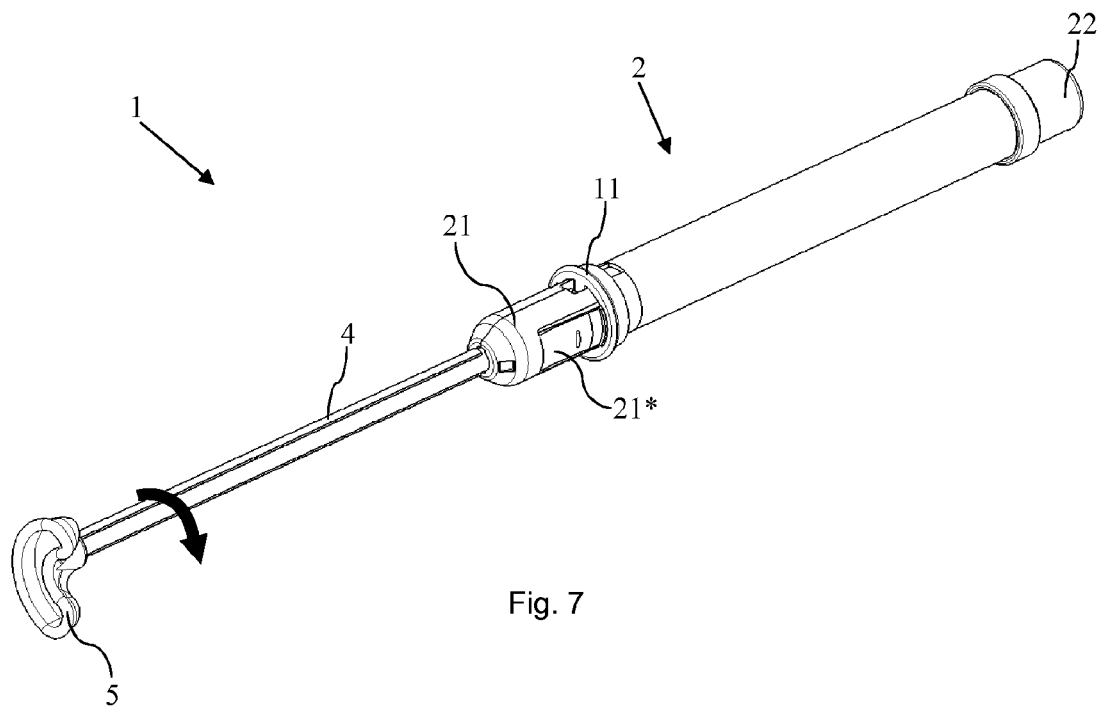
FIG. 7 shows a step of locking the rod unit of the gynecological device of FIG. 6 by a rotation of the cervix head.

FIG. 7 shows a step of locking the rod unit 4 of the gynecological device 1 by a rotation of the cervix head 5, thereby making the protrusions 44 engage with the female recesses of the front cap 21.

Figure 8:
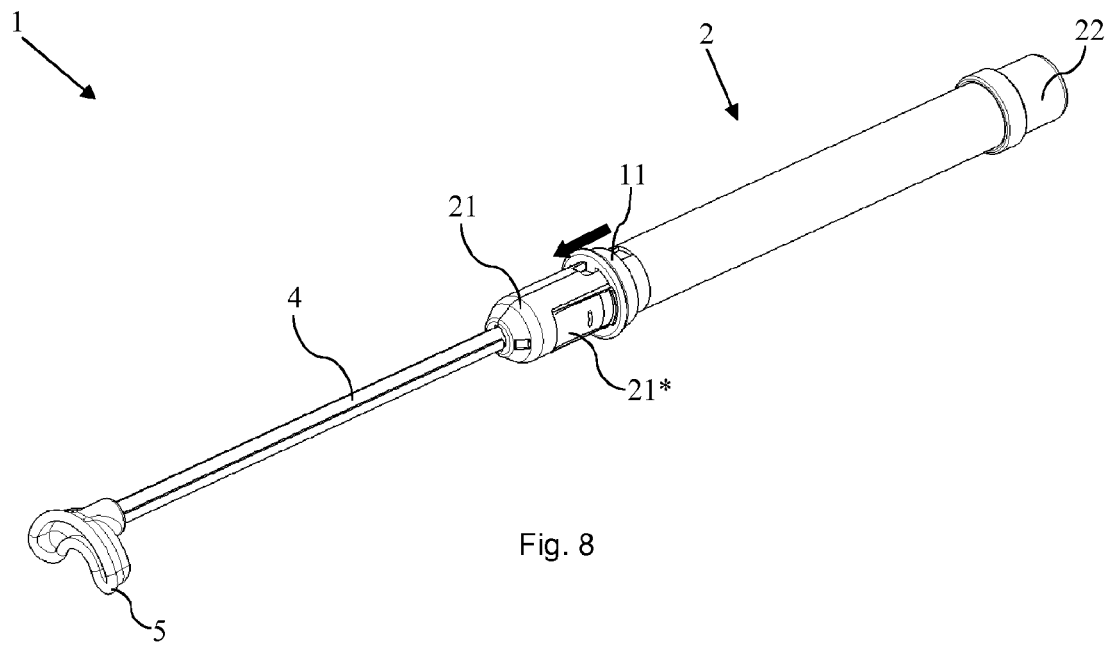
FIG. 8 shows a step of activating the vacuum created in the gynecological device of FIG. 6 by laterally sliding the activation part of FIG. 5.

FIG. 8 shows a step of activating the vacuum created in the gynecological device 1 by laterally sliding the activation part, or slider, 11.

Figure 9:
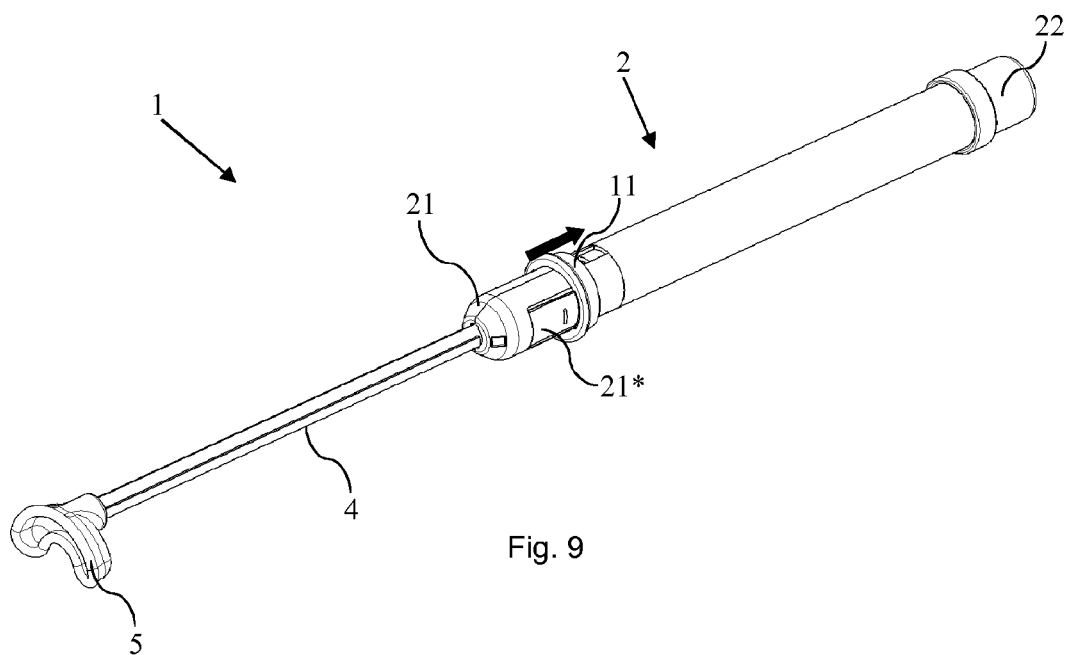
FIG. 9 shows a step of de-activating the vacuum created in the gynecological device of FIG. 6 by proximally sliding the activation part of FIG. 5.

FIG. 9 shows a step subsequent to the use of the gynecological device 1 for aligning the cervix and therefore to the completion of the cervix manipulation—of de-activating the vacuum created in the device 1 by proximally sliding the activation part, or slider, 11.

Figure 10:
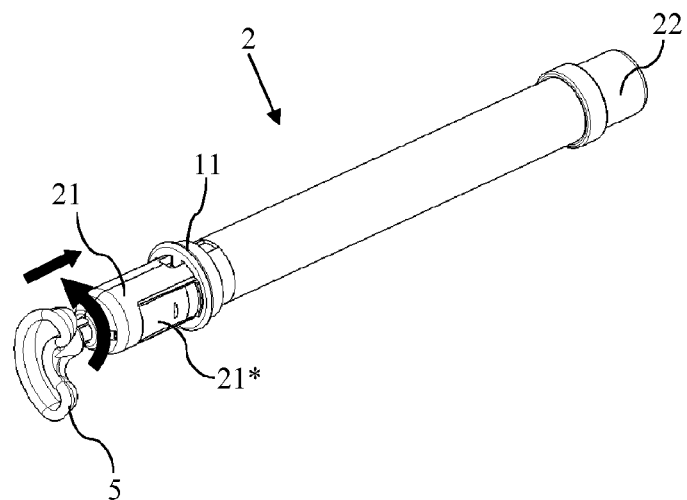
FIG. 10 shows a step of concluding a cervix head handling procedure by the gynecological device of FIG. 6 by a counter-rotation of the cervix head to unlock the rod unit and by pushing the rod unit in a proximal direction back inside the body part of the gynecological device.

FIG. 10 shows a step of concluding a cervix head handling procedure by the gynecological device 1 by a counter-rotation of the cervix head 5 to unlock the rod unit 4 and by pushing the rod unit 4 in a proximal direction back inside the body part 2 of the gynecological device 1.

Figure 11:
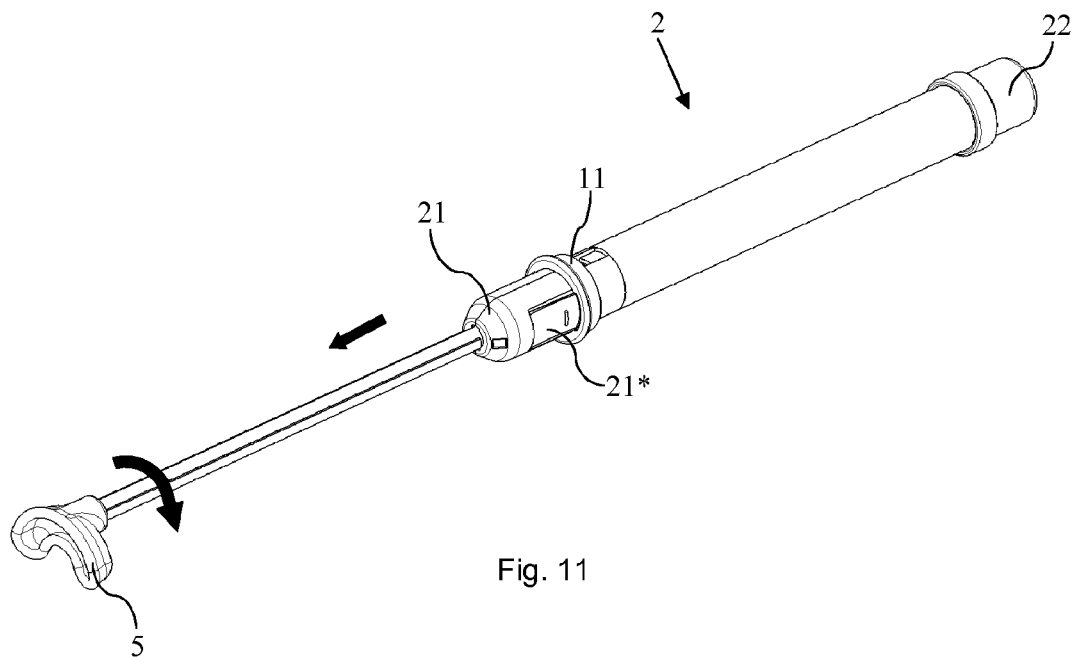
FIG. 11 shows a step of creating a new a vacuum in the gynecological device of FIG. 6 by reiterating the cervix head traction and rod unit translation, followed by locking of the rod unit analogously to the step of FIG. 7.

FIG. 11 shows a step of creating a new a vacuum in the gynecological device 1 by reiterating the cervix head traction and rod unit translation, followed by locking of the rod unit analogously to the step of FIG. 7. The same device 1 allows to carry out a new procedure on the cervix in case the first manipulation needs to be retouched or repeated or another manipulation should be performed.

Figure 12:
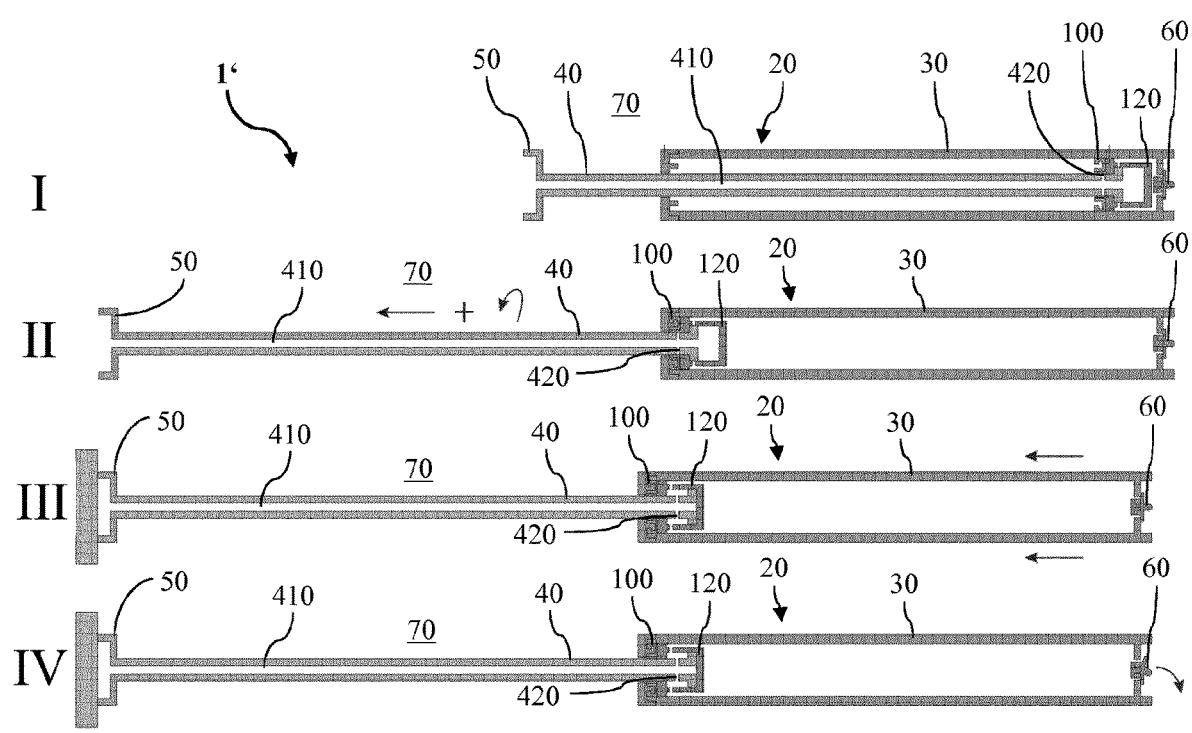
FIG. 12 shows four schematic section views of a second embodiment of the gynecological device according to the present invention illustrating a full functioning cycle thereof.

In FIG. 12 a second embodiment of a gynecological device 1' according to the present invention is shown. The gynecological device 1' is widely similarly embodied as the gynecological device 1 shown in the previous FIGS. such that for aspects not explicitly mentioned in the following description it is referred to the above description. The gynecological device 1' comprises a cylindrical body part 20 having a vacuum chamber 30, a rod unit 40 with a distal end, a proximal end and a channel 410 extending between the distal end and the proximal end. The rod unit 40 extends to the vacuum chamber 30 such that the proximal end of the rod unit 40 is located in the vacuum chamber 30. The rod unit 40 is essentially cylindrical and has a straight shape. The channel 410 is straight along the rod unit 40. The proximal end of the rod unit is provided with a cap 120 closing the channel 410 of the rod unit 40 at its proximal end. The cap 120 is equipped with a seal member 100 sealing the rod unit to a wall of the vacuum chamber 30.

A cervix head 50, designed to engage a section of a cervix from a vaginal side and to conform to its anatomy, is arranged at the distal end of the rod unit 40 to be in fluid communication with the channel 410. The rod unit is further provided with lateral through holes 420 radially opening the channel 410 near the cap 120.

The body part 20 of the gynecological device 1' comprises a releasable elastic back cap 60 tightly closing a back end of the body part 20. The body part 20 further comprises a front cap distally closing a front end. The front cap cooperates with the rod unit 40 to guide a translation movement of the rod unit 40. A sealing mechanism is configured to switch between an ambient state and a vacuum state as described in the following.

Depicted at I in FIG. 12 the gynecological device 1' is in an initial position or pre-operation state as it may be delivered to a practitioner for use. The rod unit 40 is arranged in a maximum right side position such that its cap 120 is adjoining to the elastic back cap 60. In this position, the through holes 420 of the rod unit 40 are covered and sealed by the seal member 100. In the initial position, the gynecological device 1' is in a released vacuum state in which the rod unit 40 is axially movable relative to the vacuum chamber 30.

As depicted at II in FIG. 12, for generating a vacuum inside the vacuum chamber 30, the rod unit 40 is distally moved to a maximum left side. Thereby, the cap 120 shift the sealing member 100 towards the distal end of the body part 20. The sealing member 100 still seals the rod unit 40 to the wall of the vacuum chamber, and covers and seals the through holes 420. In this position, the rod unit 40 is rotated by 90° about its longitudinal axis such that it is axially locked, i.e. not shiftable in an axial direction. The gynecological device 1' is now in a closed vacuum position. In the closed vacuum position the gynecological device 1' is in a locked vacuum state, in which the rod unit 40 cannot be moved to the ambient state of the gynecological device 1'. In particular, the locked state prevents that, due to the underpressure inside the vacuum chamber, the rod unit 40 is sucked into the vacuum chamber 30 and, thereby, axially moved to the right.

As depicted at III in FIG. 12, the cervix head 50 is located at a vaginal side of a cervix. At the same time, a push force is axially applied to the rod unit 40 such that it is slightly shifted to the right. Thereby, the though holes 420 are moved relative to the sealing member 100 such that they are opened towards the interior of the vacuum chamber 30. The vacuum is applied through the channel 410 to the cervix which is sucked and safely held at the cervix head 50. The gynecological device 1' is now in a open vacuum position, in which the gynecological device 1' still is in the locked vacuum state.

As depicted at IV of FIG. 12, for releasing the cervix the elastic back 60 is removed such that an exterior 70 is in fluid communication with the cervix via the vacuum chamber 30 and the channel 410 of the rod unit. Thereby, the vacuum is abolished and the gynecological device 1' can conveniently be removed from the cervix. The gynecological device 1' is now in an end position in an ambient state.

This description and the accompanying drawings that illustrate aspects and embodiments of the present invention should not be taken as limiting the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the FIGS. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. A gynecological device comprising:
a body part having a vacuum chamber;
a rod unit with a distal end, a proximal end, and a channel extending between the distal end and the proximal end;
a cervix head arranged at the distal end of the rod unit; and
a sealing mechanism configured to switch between an ambient state and a vacuum state,
wherein the rod unit extends to the vacuum chamber of the body part such that the proximal end of the rod unit is located in the vacuum chamber of the body part,
wherein the cervix head is configured to engage a section of a cervix from a vaginal side,
wherein the sealing mechanism is configured such that:
in the ambient state of the sealing mechanism, the vacuum chamber of the body part is sealed and the channel of the rod unit is open to an exterior of the gynecological device such that a vacuum is generatable inside the vacuum chamber,
in the vacuum state of the sealing mechanism, the channel of the rod unit is open to the vacuum chamber of the body part and sealed to the exterior of the gynecological device such that a vacuum is applied at the cervix head, when being set to the cervix through a vagina, for gripping and/or pulling the cervix, and
by changing from the vacuum state to the ambient state of the sealing mechanism again, the cervix head is releasable from the cervix by eliminating the vacuum in the cervix head,
wherein the sealing mechanism comprises a sleeve element arranged in the vacuum chamber of the body part, and the sleeve element comprises an activation part extending to an exterior of the body part,
wherein the rod unit extends through the sleeve element, and
wherein the sleeve element is axially movable relative to the vacuum chamber and relative to the rod unit along an axis of the rod unit and/or of the gynecological device.

2. The gynecological device of claim 1, wherein the sleeve element of the sealing mechanism has an internal seal member that is configured to seal the sleeve element and the rod unit towards each other.

3. The gynecological device of claim 2, wherein the sleeve element of the sealing mechanism has an external seal member sealing the sleeve element and the vacuum chamber of the body part towards each other.

4. The gynecological device of claim 3, wherein a first friction force between the internal seal member of the sleeve element of the sealing mechanism and the rod unit is smaller than a second friction force between the external seal member of the sleeve element of the sealing mechanism and the vacuum chamber of the body part.

5. The gynecological device of claim 3, wherein the internal seal member and the external seal member of the sleeve element of the sealing mechanism are axially offset from each other along the axis, wherein the internal seal member of the sleeve element of the sealing mechanism is closer to the distal end of the rod unit than the external seal member of the sleeve element of the sealing mechanism.

6. The gynecological device of claim 2, wherein in the ambient state of the sealing mechanism, the sleeve element is axially moved in a first position in which the internal seal member seals the channel of the rod unit and the vacuum chamber of the body part towards each other, and an external seal member seals the vacuum chamber of the body part towards the exterior of the gynecological device.

7. The gynecological device of claim 2, wherein in the vacuum state of the sealing mechanism, the sleeve element is axially moved in a second position in which the internal seal member seals the channel of the rod unit towards the exterior of the gynecological device, and an external seal member seals the vacuum chamber of the body part towards the exterior of the gynecological device.

8. The gynecological device of claim 1, wherein the rod unit has a projection configured to abut the sleeve element when the rod unit is moved in a distal direction along its axis through the sleeve element, wherein the projection of the rod unit is positioned such that the rod unit is movable to a predefined extent along its axis through the sleeve element.

9. The gynecological device of claim 1, wherein the rod unit has a lateral through hole open to the channel of the rod unit.

10. The gynecological device of claim 1, comprising a cap closing the channel of the rod unit at the proximal end of the rod unit.

11. The gynecological device of claim 10,
wherein the sealing mechanism comprises a sleeve element arranged in the vacuum chamber of the body part,
wherein the rod unit extends through the sleeve element,
wherein the sleeve element is axially movable relative to the vacuum chamber of the body part and relative to the rod unit along an axis of the rod unit and/or of the gynecological device, and
wherein the cap is dimensioned not to fit into the sleeve element of the sealing mechanism.

12. The gynecological device of claim 1, further comprising a locking mechanism comprising a protrusion and a corresponding recess, the locking mechanism configured to switch between a released state in which the rod unit is axially movable relative to the vacuum chamber of the body part and a locked state in which movement of the rod unit into the ambient state is prevented, wherein, in the released state of the locking mechanism, the rod unit is axially movable relative to the vacuum chamber of the body part, such that a vacuum is generated inside the vacuum chamber when the rod unit is distally moved relative to the vacuum chamber, and in the locked state the rod unit is prevented from being sucked back to an initial position of the rod unit by the generated vacuum of the vacuum chamber.

13. The gynecological device of claim 12, wherein the locking mechanism is configured such that pivoting the rod unit about its longitudinal axis in one direction switches the locking mechanism into the locked state and pivoting the rod unit about its axis in another opposite direction switches the locking mechanism into the released state.

14. The gynecological device of claim 12, wherein the rod unit has a lateral through hole open to the channel of the rod unit and the gynecological device is configured to open the through hole to the vacuum chamber of the body part when being in the locked state.

15. The gynecological device of claim 14, wherein the through hole is open to the vacuum chamber of the body part when being in the released state, and/or the gynecological device is configured to open the through hole by applying a push force to the cervix head.

16. The gynecological device of claim 1, the gynecological device being configured to be arranged in a pre-operation state in which the rod unit is moved to a maximum extent in a proximal direction into the vacuum chamber of the body part, wherein the vacuum chamber of the body part has a main section and a proximal section, the main section having a first diameter and the proximal section having a second diameter that is bigger than the first diameter.

17. The gynecological device of claim 16, wherein in an inclined transition section between the proximal section of the vacuum chamber of the body part and the main section of the vacuum chamber of the body part a diameter decreases from the second diameter to the first diameter.

18. The gynecological device of claim 1, configured to be arranged in a pre-operation state in which the rod unit is moved to a maximum extent in a proximal direction into the vacuum chamber of the body part, wherein the vacuum chamber of the body part has a main section and a proximal section, the main section having a first diameter and the proximal section having a second diameter that is bigger than the first diameter,
    wherein the sleeve element of the sealing mechanism has an internal seal member sealing the sleeve element and the rod unit towards each other, and an external seal member sealing the sleeve element and the vacuum chamber of the body part towards each other, and
    wherein the external seal member is compressed when being positioned in the main section of the vacuum chamber of the body part, and the external seal member is non-compressed when being positioned in the proximal section of the vacuum chamber of the body part.

19. The gynecological device of claim 1, wherein a friction reduction substance is provided between an internal seal member of the sleeve element of the sealing mechanism and the rod unit, wherein the friction reduction substance comprises a silicone oil.

\* \* \* \* \*